(12) United States Patent
Thym et al.

(10) Patent No.: US 7,766,845 B2
(45) Date of Patent: Aug. 3, 2010

(54) DISPOSABLE LANCET AND LANCING CAP COMBINATION FOR INCREASED HYGIENE

(75) Inventors: Detlef Thym, Mannheim (DE); Jeffrey N. Roe, San Ramon, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 212 days.

(21) Appl. No.: 10/872,945

(22) Filed: Jun. 21, 2004

(65) Prior Publication Data

US 2005/0283094 A1 Dec. 22, 2005

(51) Int. Cl.
*A61B 5/00* (2006.01)
*A61B 17/14* (2006.01)
*A61B 17/32* (2006.01)
*B65D 81/00* (2006.01)

(52) U.S. Cl. ............... 600/583; 600/584; 600/573; 606/181

(58) Field of Classification Search .............. 600/573, 600/576, 583, 584; 606/181, 182
See application file for complete search history.

(56) References Cited

U.S. PATENT DOCUMENTS

| | | | |
|---|---|---|---|
| 4,360,016 A | 11/1982 | Sarrine | |
| 4,416,279 A * | 11/1983 | Lindner et al. | 606/182 |
| 4,637,403 A | 1/1987 | Garcia et al. | |
| 4,653,513 A | 3/1987 | Dombrowski | |
| 4,677,979 A * | 7/1987 | Burns | 606/172 |
| 4,850,973 A | 7/1989 | Jordan et al. | |
| 4,858,607 A | 8/1989 | Jordan et al. | |
| 4,869,249 A | 9/1989 | Crossman et al. | |
| 4,889,117 A | 12/1989 | Stevens | |
| 4,895,147 A * | 1/1990 | Bodicky et al. | 606/182 |
| 4,920,977 A | 5/1990 | Haynes | |
| 4,924,879 A | 5/1990 | O'Brien | |
| 5,054,499 A | 10/1991 | Swierczek | |
| 5,217,480 A * | 6/1993 | Haber et al. | 606/182 |
| 5,318,584 A | 6/1994 | Lange et al. | |
| 5,320,607 A | 6/1994 | Ishibashi | |
| 5,324,303 A | 6/1994 | Strong et al. | |
| 5,368,047 A | 11/1994 | Suzuki et al. | |
| 5,402,798 A | 4/1995 | Swierczek et al. | |
| 5,439,473 A * | 8/1995 | Jorgensen | 606/182 |
| 5,554,166 A | 9/1996 | Lange et al. | |
| 5,582,184 A | 12/1996 | Erickson et al. | |

(Continued)

FOREIGN PATENT DOCUMENTS

DE    101 42 232 A1    3/2003

(Continued)

*Primary Examiner*—Max Hindenburg
*Assistant Examiner*—H. Q. Nguyen
(74) *Attorney, Agent, or Firm*—Woodard, Emhardt, Moriarty, McNett & Henry LLP

(57) ABSTRACT

A body fluid testing device includes a test strip, an incision forming member, and a housing. The test strip includes an expression surface. In addition, the test strip is attached to the housing to form a cavity, and the cavity slidably receives the incision forming member. The body fluid testing device is positioned over the incision site where the incision forming member makes an incision. The user presses the expression surface against the skin to express body fluid. The cavity collects body fluid via capillary action, and the test strip analyzes the body fluid.

17 Claims, 12 Drawing Sheets

U.S. PATENT DOCUMENTS

| | | | |
|---|---|---|---|
| 5,628,764 A | 5/1997 | Schraga | |
| 5,700,695 A * | 12/1997 | Yassinzadeh et al. | 436/180 |
| 5,741,288 A * | 4/1998 | Rife | 606/181 |
| 6,149,608 A * | 11/2000 | Marshall et al. | 600/573 |
| 6,228,100 B1 | 5/2001 | Schraga | 606/183 |
| 6,299,626 B1 * | 10/2001 | Viranyi | 606/182 |
| 6,315,738 B1 * | 11/2001 | Nishikawa et al. | 600/583 |
| 6,322,574 B1 | 11/2001 | Lloyd et al. | |
| 6,322,575 B1 | 11/2001 | Schraga | |
| 6,358,265 B1 * | 3/2002 | Thorne et al. | 606/181 |
| 6,514,270 B1 | 2/2003 | Schraga | |
| 6,540,762 B1 | 4/2003 | Bertling | |
| 6,561,989 B2 * | 5/2003 | Whitson | 600/573 |
| 6,576,101 B1 * | 6/2003 | Heller et al. | 204/403.14 |
| 6,696,024 B1 | 2/2004 | Leichner et al. | |
| 6,958,072 B2 * | 10/2005 | Schraga | 606/182 |
| 6,997,936 B2 * | 2/2006 | Marshall | 606/181 |
| 2001/0041904 A1 * | 11/2001 | Heller et al. | 606/181 |
| 2002/0004196 A1 | 1/2002 | Whitson | |
| 2002/0016606 A1 | 2/2002 | Moerman | |
| 2002/0087180 A1 | 7/2002 | Searle et al. | |
| 2002/0120216 A1 * | 8/2002 | Fritz et al. | 600/583 |
| 2002/0151920 A1 | 10/2002 | Marshall et al. | |
| 2002/0168290 A1 | 11/2002 | Yuzhakov et al. | |
| 2003/0050573 A1 | 3/2003 | Kuhr et al. | |
| 2003/0100913 A1 | 5/2003 | Shi | |
| 2003/0109777 A1 | 6/2003 | Kloepfer et al. | |
| 2003/0109895 A1 * | 6/2003 | Taylor et al. | 606/181 |
| 2003/0144608 A1 * | 7/2003 | Kojima et al. | 600/583 |
| 2003/0144609 A1 * | 7/2003 | Kennedy | 600/583 |
| 2004/0064068 A1 * | 4/2004 | DeNuzzio et al. | 600/583 |
| 2004/0127818 A1 * | 7/2004 | Roe et al. | 600/583 |
| 2004/0127929 A1 * | 7/2004 | Roe | 606/181 |
| 2004/0138588 A1 * | 7/2004 | Saikley et al. | 600/583 |
| 2004/0186394 A1 * | 9/2004 | Roe et al. | 600/583 |
| 2004/0215224 A1 * | 10/2004 | Sakata et al. | 606/181 |
| 2004/0236251 A1 * | 11/2004 | Roe et al. | 600/583 |
| 2005/0096565 A1 * | 5/2005 | Chang | 600/584 |
| 2005/0277850 A1 | 12/2005 | Mace et al. | |
| 2005/0283177 A1 * | 12/2005 | Chen | 606/181 |

FOREIGN PATENT DOCUMENTS

| | | |
|---|---|---|
| EP | 0 199 484 A2 | 10/1986 |
| EP | 1 035 919 B1 | 9/2000 |
| EP | 1 035 920 B1 | 9/2000 |
| EP | 1 285 629 A1 | 2/2003 |
| EP | 1 402 812 A1 | 3/2004 |
| WO | WO 02/056751 A2 | 7/2002 |
| WO | WO 2004/066822 A2 | 8/2004 |

* cited by examiner

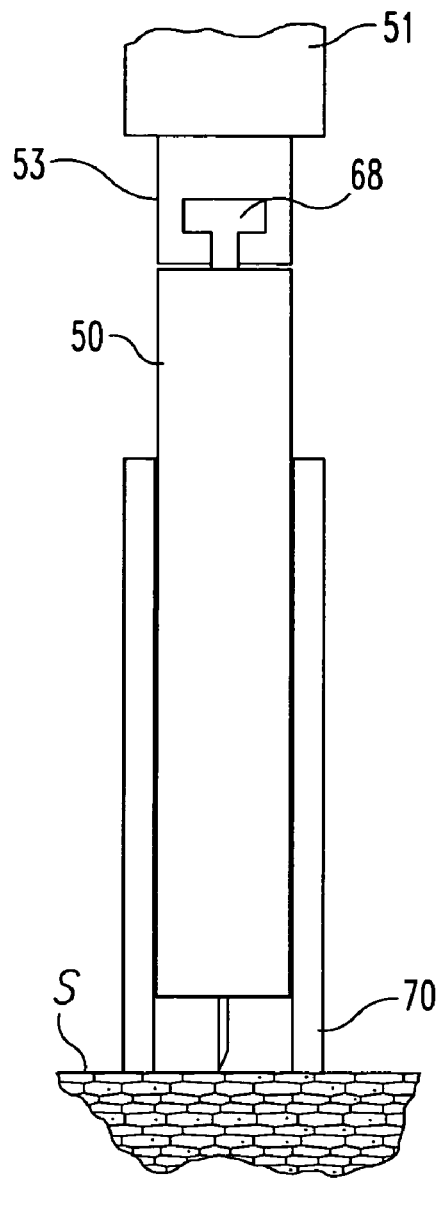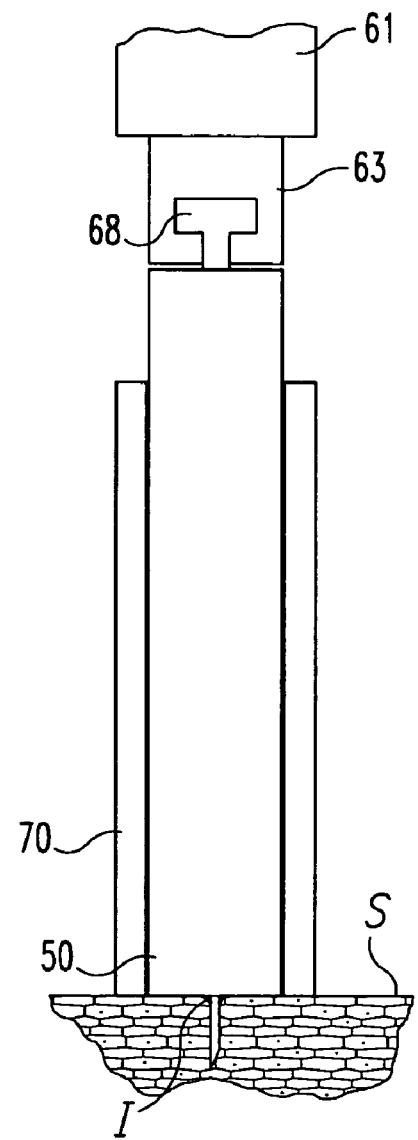
Fig. 23    Fig. 24

DISPOSABLE LANCET AND LANCING CAP COMBINATION FOR INCREASED HYGIENE

BACKGROUND OF THE INVENTION

The present invention generally relates to body fluid sampling devices, and more specifically, but not exclusively, concerns a disposable lancet and lancing cap sampling device and a technique for sampling fluid with the device.

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

For example, a common medical test is the measurement of blood glucose levels for diabetes. Diabetics must test their blood glucose levels several times a day. The glucose level can be determined directly by the analysis of a blood sample, or indirectly by analysis of other fluids, such as interstitial fluid. Other medical tests may analyze a body fluid sample for a variety of properties or components, as is well known in the art. For example, such analysis may be directed to hematocrit, cholesterol, uric acid, coagulation, etc.

The testing of bodily fluids basically involves the steps of obtaining the fluid sample, transferring the sample to a test device, conducting a test on the fluid sample, and displaying the results. These steps are generally performed by a plurality of separate instruments or devices.

In one form, a body fluid sampling device is composed of a lancet to form an incision and a microcollection tube to collect the body fluid. However, the lancing and collection are two separate activities requiring hand coordination and dexterity to perform both activities. Often this is difficult for those persons that are elderly or young.

Another form of collecting a body fluid sample is with a suction-type blood sampler. This device develops suction between a lancing site and the end of the device when the lancet holding mechanism withdraws after piercing the skin. A flexible gasket around the end of the device helps seal the end around the puncture site while the user attempts to draw a sample from the puncture site or the user pulls back on the device to release the seal. A diaphragm over the puncture site can also create a vacuum. This type of device only draws bodily fluid while the device creates a vacuum with the skin to form suction pressure. However, after the air is expelled, the suction pressure will cease and no additional body fluid is collected.

An alternative form of collecting and measuring body fluids uses a coaxial syringe and capillary tube disposed within a spacer member. The spacer member limits the depth of syringe penetration, and compresses body tissue around the syringe while the syringe is in the skin, for improving the flow of interstitial fluid to the incision. However, it will be appreciated that the incision will tend to close against the syringe, thereby limiting any advantage that can be achieved.

One problem associated with some lancing devices that control or adjust the puncture depth to reduce the pain of lancing is that the blood lancet device does not collect blood from the incision.

Some forms of a disposable lancing device include a plastic injection device that may be alternatively used as a syringe-type injection device and a lancing device with a disposable solid needle lancet, depending on configuration. However, this type of device does not collect a body fluid sample.

One problem associated with some lancing devices is that the devices must be cleansed to maintain proper hygiene between uses of the instruments, and to prevent cross-contamination and/or contamination. Cross-contamination of blood samples may be a problem if more than one person uses the devices and the devices are not properly cleansed between each use. Contamination of a blood sample may be a problem if one person repeatedly uses the devices without properly cleaning the devices between each use.

In institutional settings, the bodily fluid sample is often collected from the patient and then introduced to a test device in a controlled fashion. Some blood glucose monitoring systems, for example, require that the bodily fluid sample be applied to a test disposable that is in contact with a test instrument. In such situations, bringing an incised finger or other incised body part of a patient directly to the test disposable poses some risk of contamination from bodily fluid of a previous patient. With such systems, particularly in hospital settings, a patient is lanced, a sample is collected in a micropipette via capillary action and then the sample is delivered from the pipette to the test disposable. However, this technique still produces hygiene and cross-contamination problems, and is inconvenient because it requires the use and disposal of three components, the test disposable, the lancet, and the blood collection device.

Another problem associated with some lancing devices is that fingertips are commonly lanced to obtain an adequate sample of blood and repeated lancing of fingertips can be painful due to the high concentration of nerve endings in the fingertips. Therefore, alternate sites on the body that have fewer nerve endings may provide a less painful area to sample blood or other body fluids. However, these alternate sites may produce less body fluid when lanced as compared to fingertips. Therefore, it is important to reduce the amount of fluid required for testing at an alternate site. To adequately test body fluid obtained from an alternate site, enough fluid must be expressed and collected from the incision before the fluid can be tested.

Yet another problem associated with some lancing devices and testing devices is that such devices are disposed of independently thereby creating additional hazardous waste.

Thus, there remains a need for improvement in this field.

SUMMARY

One aspect of the present invention concerns a body fluid testing device that includes a test strip mounted to a housing to form a cavity. The cavity slidably receives an incision forming member. The test strip has a skin contacting portion that contains an expression surface to express fluid from an incision.

A further aspect concerns a body fluid testing device. The device includes a housing that has an opening to receive a tab from the incision forming member. The opening controls the depth of penetration into the skin as the tab of the incision forming member glides in the opening and the incision forming member penetrates the skin.

One more aspect concerns a body fluid testing device. The device includes a housing with an extension member to contact skin and a test strip attached to the housing. The test strip and extension member define a passageway sized and arranged to draw fluid via capillary action from an incision in skin. An incision forming member forms the incision in skin and is partially received within the passageway.

Another aspect concerns a method of sampling a body fluid. The method includes providing a body fluid sampling device that includes an incision forming member, a test strip, and a housing. An incision is formed in the skin with the incision forming member. The test strip includes an expression surface that expresses the body fluid from the incision. The housing and test strip form a cavity or a passageway that collects the body fluid from the incision via capillary action. The device includes means for analyzing body fluid from the incision site. A further aspect includes disposing of the body fluid testing device.

Another aspect concerns a method of sampling a body fluid. The method includes providing a body fluid sampling device that includes an incision forming member, a test strip, and a housing. An incision is formed in the skin with the incision forming member. The housing and test strip are pressed against the skin surrounding the incision to express fluid from the incision. The housing and test strip form a cavity that collects the fluid from the incision via capillary action. The test strip analyzes the body fluid from the incision.

Further forms, objects, features, aspects, benefits, advantages, and embodiments of the present invention will become apparent from a detailed description and drawings provided herewith.

BRIEF DESCRIPTION OF THE DRAWINGS

FIG. 23 is a rotated view of the FIG. 19 device before the incision is formed in the skin.

FIG. 24 is a rotated view of the FIG. 19 device forming an incision in the skin.

DESCRIPTION OF THE SELECTED EMBODIMENTS

Figure 1:
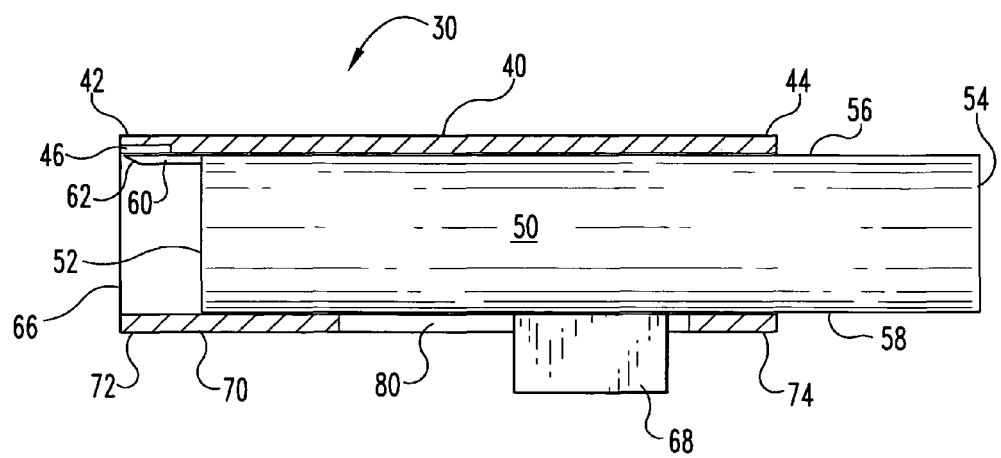
FIG. 1 is a first cross sectional view of a body fluid testing device according to one embodiment in a retracted position.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention generally concerns a disposable body fluid testing device that reduces the number of steps involved in forming, collecting, and testing a bodily fluid sample from an incision. The body fluid testing device or cartridge includes an incision forming member, a housing, and a test strip that has an expression surface. The test strip attaches to the housing to form a cavity in which the incision forming member is slidably received. In one form, the cavity is sized to draw fluid via capillary action. In another form, the test strip is configured to draw fluid via capillary action. The body fluid testing device is operable by slidably moving the incision forming member to form an incision in the skin of a person. More specifically, the body fluid testing device is operable to lance the skin with the incision forming member and express body fluid from the incision with the expression surface. The expression surface forces fluid from the incision. In another embodiment, body fluid is expressed from the incision by pressing the test strip and the housing against the skin surrounding the incision. In one embodiment, after lancing the skin the incision forming member is retracted into the cavity, body fluid is collected via capillary action by the cavity and the body fluid is tested with the test strip. In another embodiment, after lancing the skin the incision forming member is retracted into the cavity, and the test strip is configured to collect and test the body fluid from the incision. It is contemplated that for increased hygiene, in another embodiment, the body fluid testing device is disposable after testing the body fluid sample. Another body fluid testing device must be used for the next testing of a sample of body fluid. For example, after one use of the body fluid testing device the user disposes of the device and uses another body fluid testing device when the user needs to test body fluid at a later time.

A cartridge or body fluid testing device 30 according to one embodiment, among others, of the present invention will now be described with reference to FIGS. 1, 2, 3 and 4. As depicted in FIG. 1, the body fluid testing device 30 includes a test strip 40 for analyzing a bodily fluid.

In the illustrated embodiment, as depicted in FIG. 1, the test strip 40 includes a skin contacting portion 42 and a distal portion 44. The skin contacting portion 42 includes an expression surface 46 capable of expressing fluid from the incision. The expression surface 46 urges fluid from an incision site, such as by applying pressure to the area near the incision to milk or pump the fluid from the incision. The test strip 40 can analyze fluid through such means as optical (e.g., reflectance, absorption, fluorescence, RAMAN, etc.), electrochemical (e.g. amperometric, potentiometric, or coulombmetric), and/or magnetic analysis. In one embodiment, the test strip 40 analyzes fluid optically through a chemical reagent. In another embodiment, the test strip 40 analyzes fluid electrochemically through soluble chemical reagents and/or reagents fixed to an electrode. In another embodiment the test strip 40 may have another shape. For instance, the test strip 40 may include a rectangular, cylindrical, or an elliptical shape to form a test strip 40, to name a few. Test strips are available commercially, for example under the trade name ACCU-CHEK GO® from Roche Diagnostics or ACCU-CHEK COMPACT® from Roche Diagnostics.

Figure 2:
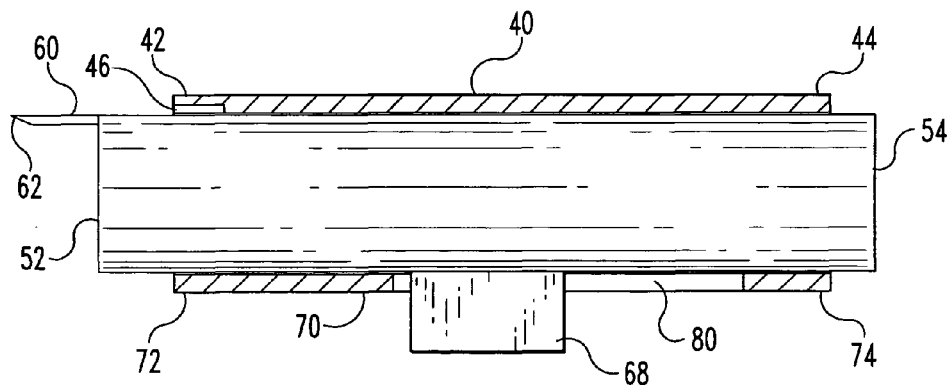
FIG. 2 is a second cross sectional view of the FIG. 1 body fluid testing device in an extended position.
Figure 4:
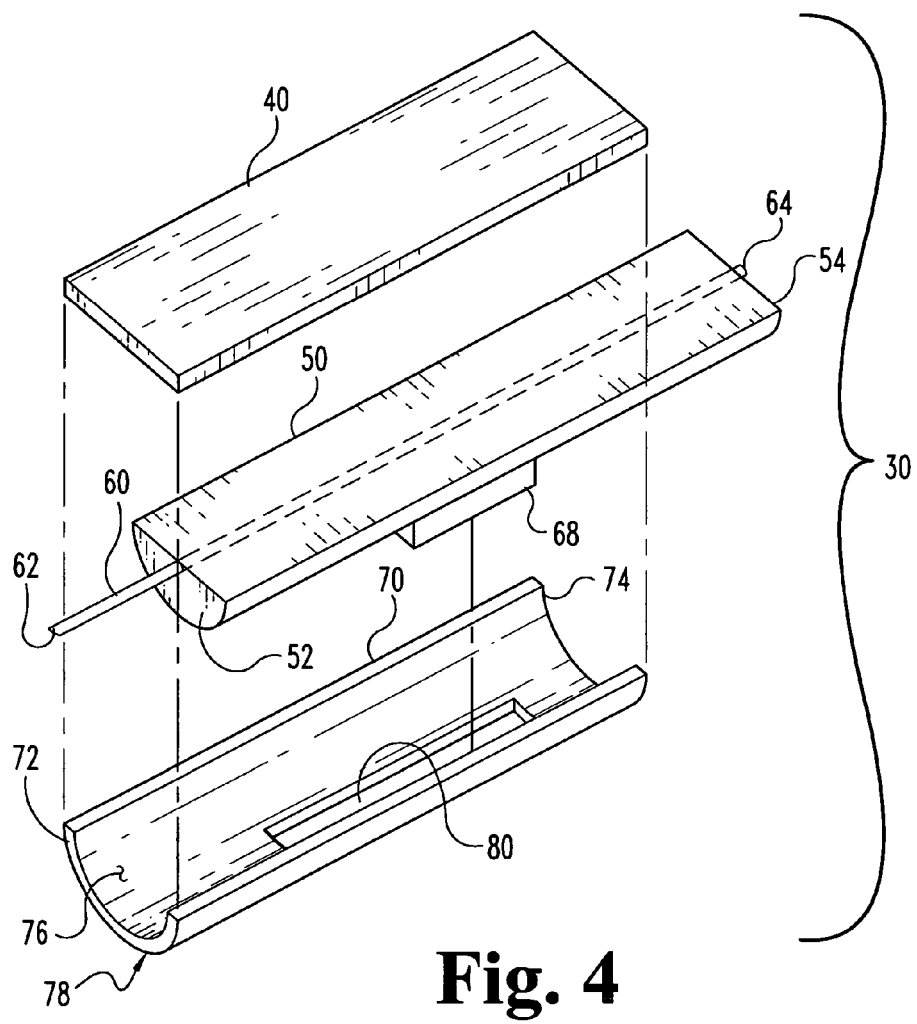
FIG. 4 is an exploded view of the FIG. 1 device.

As can be seen from FIGS. 1, 2 and 4, the body fluid testing device 30 includes an incision forming member 50 for forming an incision in the skin of a person. The incision forming member 50 includes a sampling portion 52 and an opposite end portion 54. The incision forming member 50 also includes a test strip facing surface 56 and a housing facing surface 58. In one form, the test strip facing surface 56 is coated or made with a hydrophilic material to enhance capillary action or affinity. In another form, the housing facing surface 58 is coated or made with a hydrophobic material to repel the bodily fluid towards the test strip facing surface 56. It is contemplated that in other embodiments the incision forming member 50 is coated or made with a combination hydrophobic and hydrophilic material to direct fluid towards the test strip 40. By directing fluid to the test strip 40, the amount of fluid needed for testing can be reduced. The incision forming member 50 is configured to form an incision in the skin. In the illustrated embodiment, the incision forming member 50 includes a needle 60 for forming the incision. An incision may include any opening in the skin that permits access to the bodily fluid. In the illustrated embodiment, the needle 60 forms an incision, but it should be appreciated that in other embodiments, the incision forming member 50 can include other devices to form an incision or rupture the skin. For instance, the incision forming member 50 may include a lancet, a laser, a blade, and/or a high speed fluid stream to form an incision, to name a few. The needle 60 includes a needle tip 62 for contacting the skin and a needle end 64. The incision forming member 50 is configured to slidably engage within a cavity 66. The cavity 66 encases the incision forming member 50. In one embodiment, the cavity 66 is sized to draw fluid via capillary action. In another embodiment, the cavity 66 is sized such that expression surface 46 draws fluid. Different materials may have different affinities for a fluid, such that forming the expression surface 46 and the sampling portion 52 from different materials will provide a change in the capillary affinity between those portions. Capillary affinity is also changed by treating or coating the expression surface 46, for example, to provide a resulting surface that is more or less hydrophilic. In addition, the capillary affinity is also changed by treating or coating the sampling portion 52 and/or the test strip facing surface 56 to provide a resulting surface that is more or less hydrophilic. The present invention is operable in respect to any way in which the capillary affinity is varied. In another embodiment, the incision forming member 50 has a tab 68. The tab 68 actuates the incision forming member 50 when the tab 68 is engaged by an actuation mechanism of the type as generally known by those skilled in the art. In the illustrated embodiment, the tab 68 has a generally rectangular shape, but it should be appreciated that in other embodiments, the tab 68 may be shaped differently. For instance, the tab 68 may be circular or elliptical in shape.

As depicted in FIGS. 1, 2, and 4, the body fluid testing device 30 includes a housing 70 attached to the test strip 40 that forms the cavity 66. The housing 70 includes a first portion 72 and an opposite second portion 74. As depicted in FIG. 4, the housing 70 also includes an interior surface 76 and an exterior surface 78. In one embodiment, the housing 70 includes an opening 80 that is configured to receive the tab 68 of the incision forming member 50. In the illustrated embodiment, the opening 80 has a generally rectangular shape, but it should be appreciated that in other embodiments, the opening 80 may be shaped differently. By way of nonlimiting examples, the opening 80 may be a slot, a slit, or a rectangle with rounded ends in shape, or any other shape that mates with tab 68. In the illustrated embodiment, the tab 68 glides in the opening 80. The length of the opening 80, in the illustrated embodiment is beneficial as that length determines the limits of movement of the tab 68 and the penetration depth into the skin of the person by the incision forming member 50. In another embodiment, an actuation mechanism may be coupled to the tab 68 to further limit the movement of the tab 68 in the opening 80.

The depth of penetration of the incision generally controls the fluid produced, particularly in combination with the characteristics of the incision site. The present invention is useful with various bodily fluids, including blood or interstitial fluid. The body fluid testing device may be configured for production of either blood or interstitial fluid, for example, by controlling the distance which the incision forming device extends into the skin of the user. For example, a depth of 0.25 mm to 4 mm will typically produce blood from the dermis, while a depth of 0.05 mm to 0.5 mm will produce interstitial fluid from the epidermis.

Figure 3:
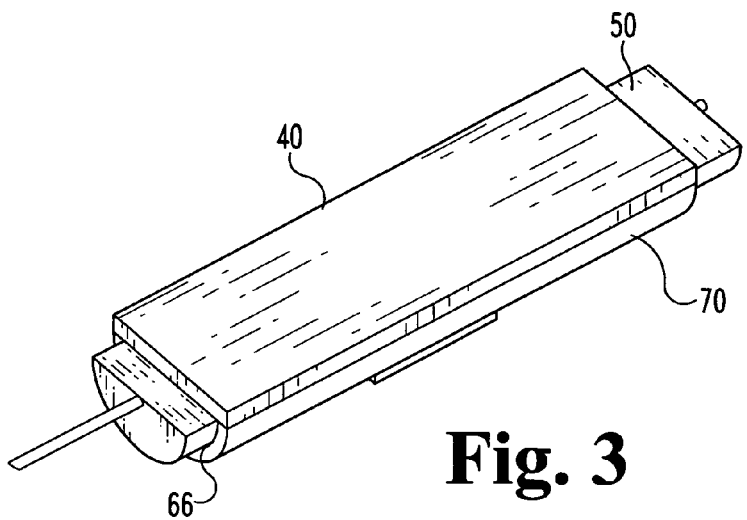
FIG. 3 is a perspective view of the FIG. 1 device.

As depicted in FIGS. 1 and 3, the test strip 40 is attached to the housing 70 such that the cavity 66 is formed in which the incision forming member 50 is slidably received. It should be appreciated, however, that the test strip 40 can be attached to the housing 70 in other manners. By way of nonlimiting examples, the test strip 40 can be attached to the housing 70 through an adhesive, a clamp mechanism, welded, and/or by a snap mechanism, to name a few. Still further, the test strip 40 and the housing 70 could be molded as one body instead of two separate attachable elements. In the illustrated embodiment, the housing 70 has a half-pipe shape and the incision forming member 50 has a half-cylindrical shape. In the illustrated embodiment, the half-pipe shape of the housing 70 is beneficial as that shape is easy to manufacture and grasp by the user. It should be appreciated that the housing 70 and incision forming member 50 may be shaped differently in other embodiments. For instance, the housing 70 may be a rectangle receptacle and the incision forming member 50 may be rectangular in shape. In the illustrated embodiment, the cavity 66 has a half-cylindrical shape but it should be appreciated that the cavity 66 may be shaped differently in other embodiments.

As can be seen from FIGS. 3 and 4, the test strip 40 attaches to the housing 70 to align skin contacting portion 42 with first portion 72. The skin contacting portion 42 and the first portion 72 express fluid from an incision, such as by applying pressure to the area surrounding the incision to milk or pump the fluid from the incision. By way of nonlimiting examples, the skin contacting portion 42 and the first portion 72 express fluid through such means as applying pressure to the skin surrounding the incision, and/or squeezing or constricting the skin surrounding the incision.

Figure 5:
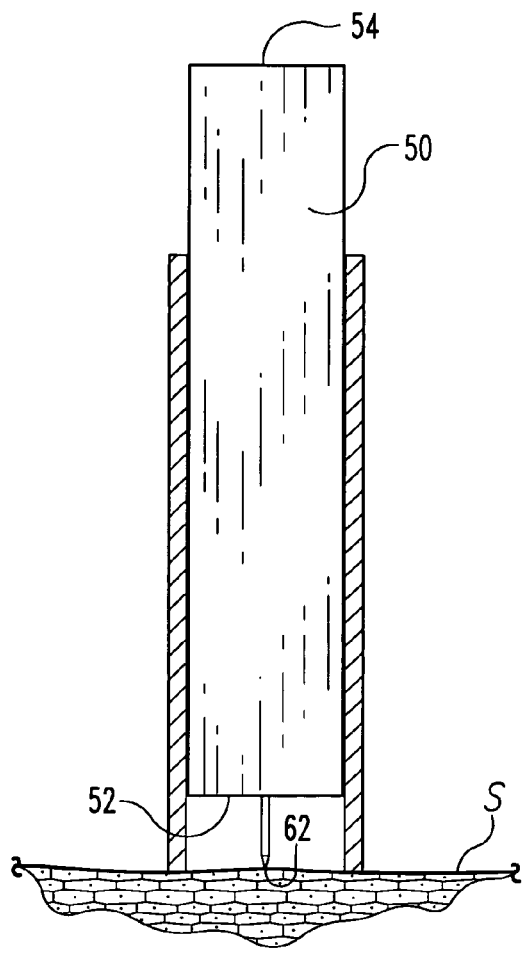
FIG. 5 is a rotated view of the FIG. 1 device before the incision is formed in the skin.
Figure 6:
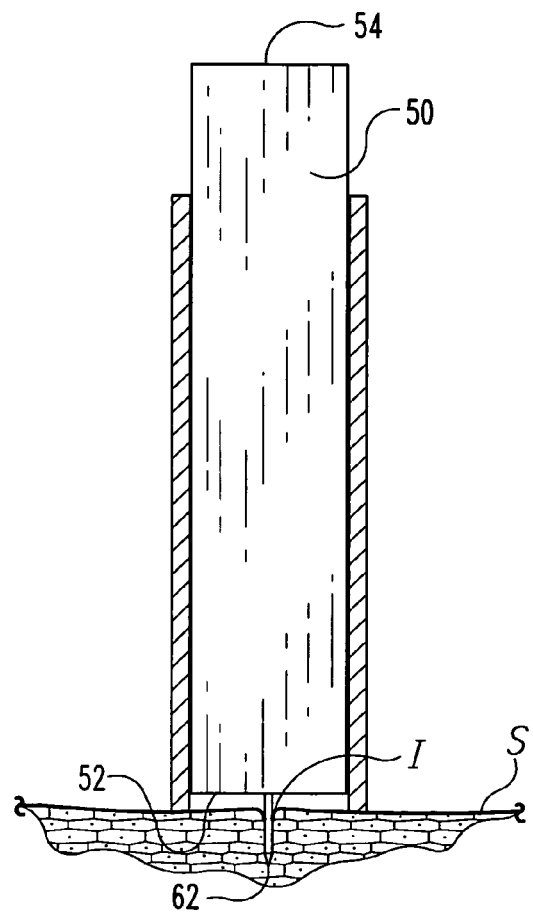
FIG. 6 is a rotated view of the FIG. 1 device forming an incision in the skin.
Figure 17:
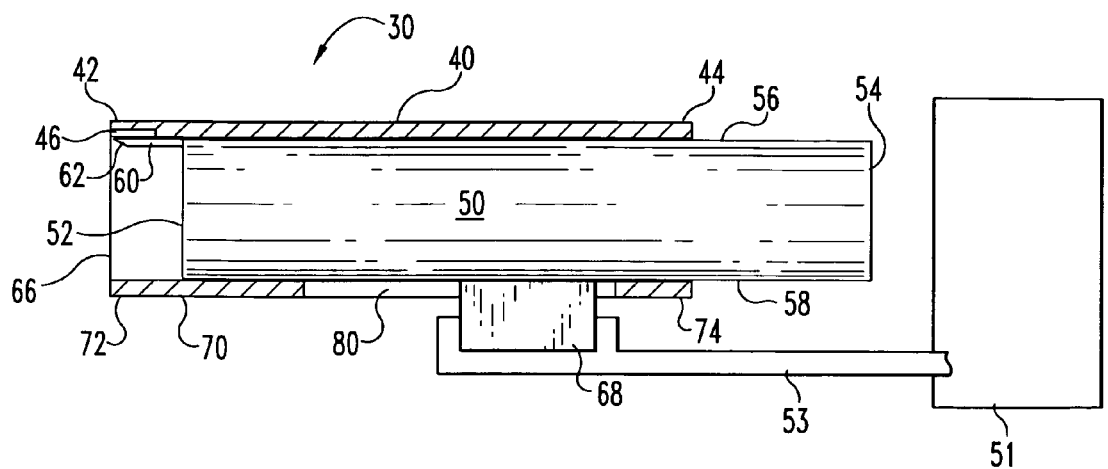
FIG. 17 is a third cross sectional view of the FIG. 1 body fluid testing device in a retracted position with a retraction mechanism.
Figure 18:
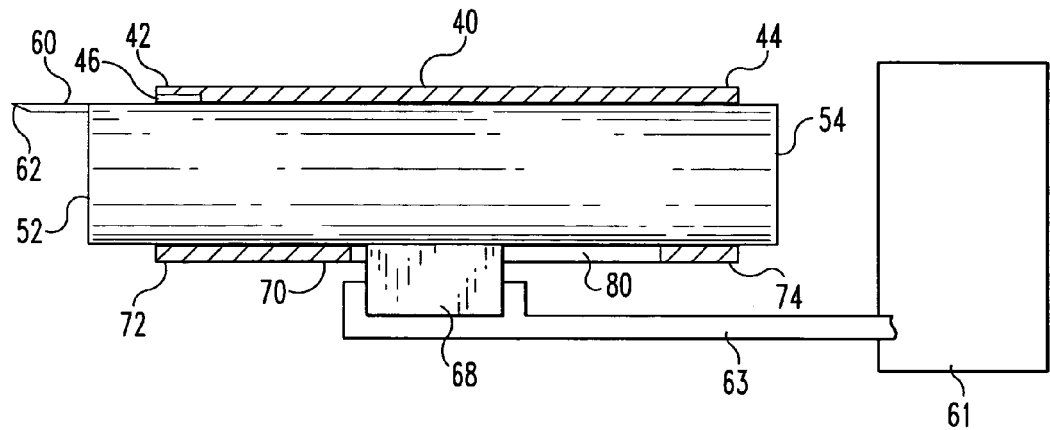
FIG. 18 is a fourth cross sectional view of the FIG. 1 body fluid testing device in an extended position with an actuation mechanism.
Figure 19:
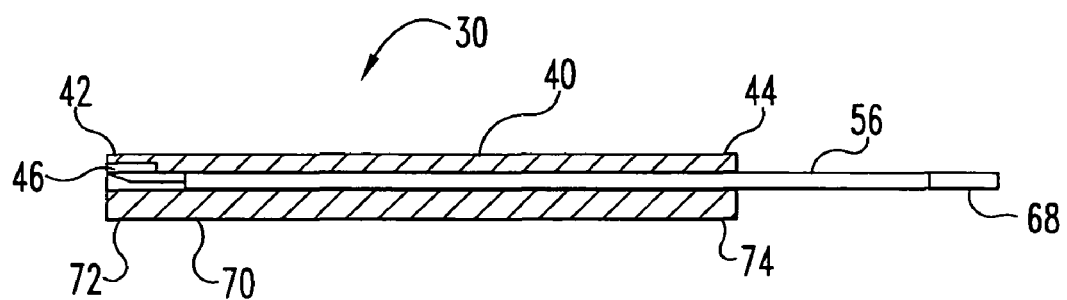
FIG. 19 is a fifth cross sectional view of the body fluid testing device according to a fifth embodiment in a retracted position.
Figure 20:
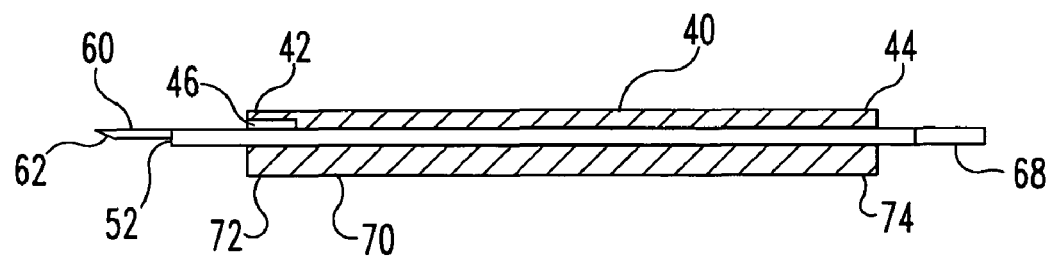
FIG. 20 is a fifth cross sectional view of the FIG. 19 body fluid testing device in an extended position.

The operation of the body fluid testing device 30 according to one embodiment will now be described with reference to FIGS. 1, 2, 5 and 6. FIGS. 1 and 5 illustrate the relative position of the incision forming member 50 such that the needle tip 62 is retracted beyond the skin contacting portion 42 towards the distal portion 44 of the test strip 40 before the body fluid testing device 30 is placed on the user's skin S. The incision forming member 50 is retracted by retraction mechanisms as shown in FIG. 17. The retraction mechanism 51 has an arm 53 that is coupled to the tab 68 to retract the incision forming member 50. In an alternate embodiment, the arm 53 of the retraction mechanism 51 is coupled to the end portion 54 to retract the incision forming member 50. The opening 80 that receives the tab 68 limits the motion or movement of the incision forming member 50. The skin contacting portion 42 is placed against the skin S. FIGS. 2 and 6 illustrate the relative position of incision forming member 50 after the end portion 54 is driven toward the sampling portion 52 thereby lancing the user's skin S with the needle tip 62 to form incision I. The incision forming member 50 can be actuated or driven towards the skin S using actuation mechanisms of a lancing device as shown in FIG. 18. The actuation mechanism 61 has an arm 63 that is coupled to the tab 68 to drive the incision forming member 50 towards the skin S. In an alternate embodiment, the arm 63 of the actuation mechanism 61 is coupled to the end portion 54 to drive the incision forming member 50 towards the skin S. After an incision I in the skin S is formed, the needle tip 62 is withdrawn from the user's skin S. FIGS. 1 and 5 also illustrate the relative position of the incision forming member 50 after the sampling portion 52 is retracted towards the end portion 54 thereby removing the needle tip 62 from the user's skin S. In one form, the incision forming member 50 can be retracted by a retraction mechanism as shown in FIG. 17. The arm 53 of the retraction mechanism 51 is attached to the tab 68 to move the tab 68 within the opening 80 thereby retracting the incision forming member 50. In another form, the arm 53 of the retraction mechanism 51 is attached to the end portion 54 to retract the incision forming member 50.

Figure 7:
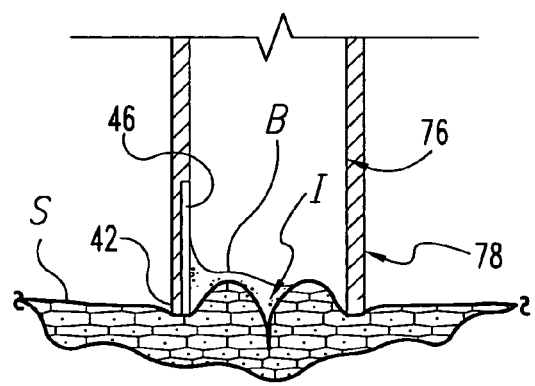
FIG. 7 is a rotated view of the FIG. 1 device during expression of fluid from the skin.

FIG. 7 illustrates expressing bodily fluid from incision I according to one embodiment where the skin contacting portion 42 remains in contact with the skin S. After the sampling portion 52 is retracted from the skin S, the body fluid B is expressed from the incision I. In one form, the expression surface 46 is pressed against the skin S to urge fluid B from the incision I. In another form, the skin contacting portion 42 of the test strip 40 and the first portion 72 of the housing 70 are pressed against the skin S to urge fluid B from the incision I. The skin contacting portion 42 and the first portion 72 express fluid B from the incision I, such as by applying pressure to the skin S surrounding the incision I to milk or pump the fluid B from the incision I. In one form, after the body fluid B is expressed, the cavity 66 collects fluid B from the incision I via capillary action. The body fluid B is also drawn onto the test strip 40 for testing via the capillary action of the cavity 66. In another form, after the body fluid B is expressed, the expression surface 46 of test strip 40 is configured to collect the body fluid B. Further, the expression surface 46 is coated with a hydrophilic material to collect body fluid B via capillary action.

As should be appreciated, the body fluid testing device 30 illustrated in FIGS. 1, 2, 5, 6 and 7 improves the speed and ease of use for a device that simultaneously expresses and collects bodily fluid for testing. With the expression surface 46 and the cavity 66 combined into one device, the user will quickly be able to express and collect bodily fluid. It should be appreciated that the body fluid testing device 30 is useful for alternate site testing where enough fluid must be expressed and collected from the incision to test the fluid. In one embodiment, the body fluid testing device 30 is disposable thus leaving the retraction mechanism and/or the actuation mechanism for a later use with another body fluid testing device 30. In the illustrated embodiment, the body fluid testing device 30 is disposed as a single unit thereby reducing the hazardous waste.

Figure 8:
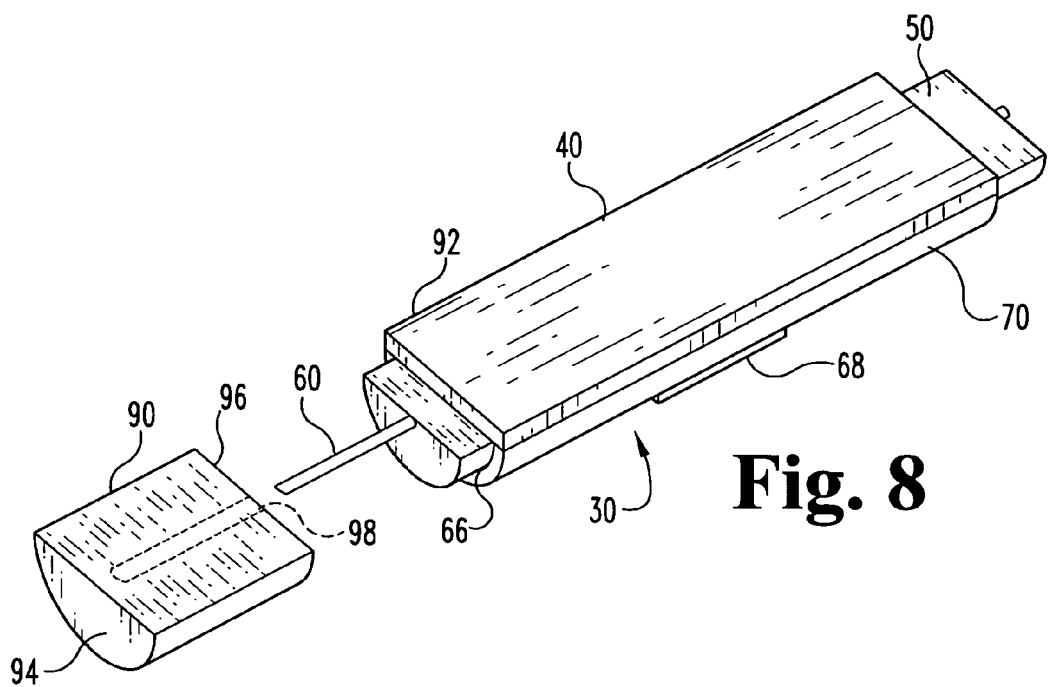
FIG. 8 is a perspective view of a body fluid testing device according to a second embodiment.
Figure 9:
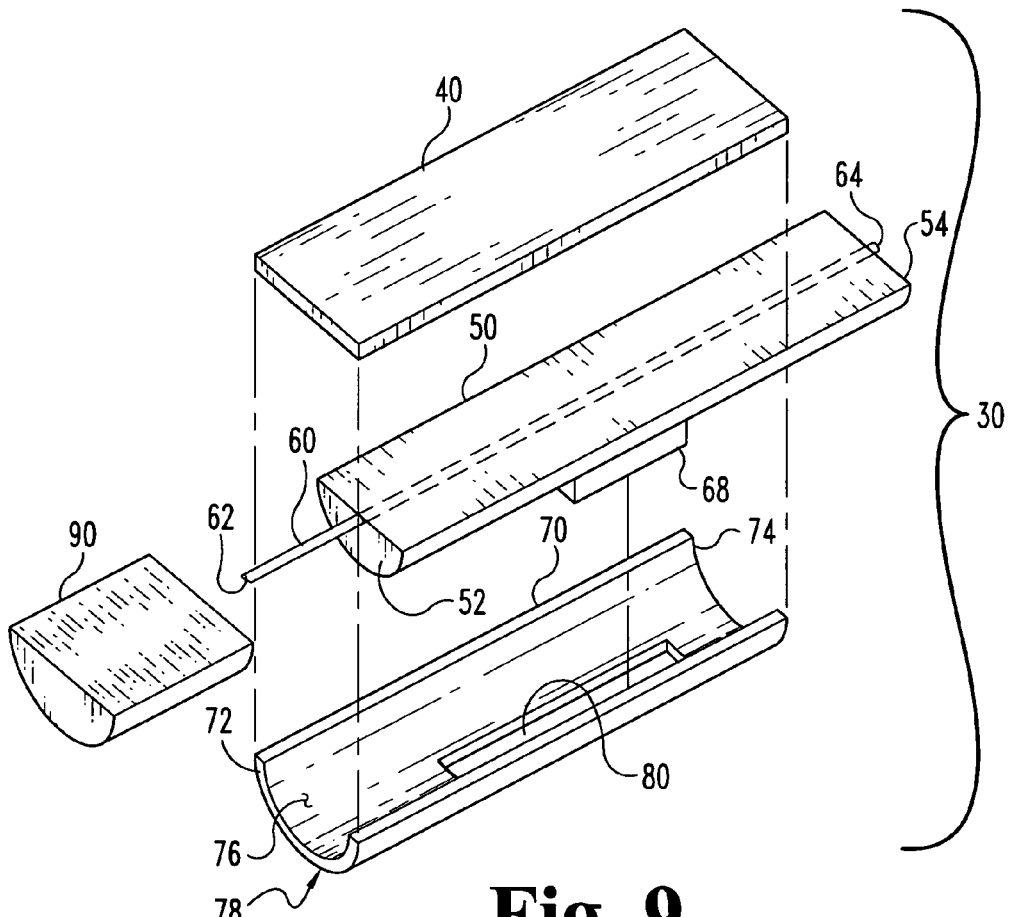
FIG. 9 is an exploded view of the FIG. 8 device.

In one embodiment, illustrated in FIGS. 8 and 9, the body fluid testing device 30 includes an end cap 90 to detachably cover a front portion 92 of the testing device 30. The end cap 90 includes a forward end wall 94 opposite a rear end 96 configured to store the front portion 92. In the illustrated embodiment, the end cap 90 is a half-cylindrical shape. In other forms, the end cap 90 may be rectangular, oval, ellipitical, or any other shape that matches the front portion 92. The rear end 96 includes an opening 98 for storing the needle tip 62 and the needle 60. Various configurations can be used to attach end cap 90 to front portion 92. For example, end cap 90 may be pushed onto front portion 92. To use the testing device 30, the end cap 90 is removed from the front portion 92. In one form the end cap 90 may be detached from the front portion 92 by turning, rotating, or pulling the end cap 90 relative to the front portion 92. As should be appreciated, other forms of attaching and/or detaching end cap 90 from front portion 92 may be used.

It should be appreciated that the placement of the end cap 90 onto the front portion 92 protects the sterility of the needle tip 62 and the needle 60. Further, the end cap 90 is detached from the front portion 92 to expose needle tip 62 for use. After use of the body fluid testing device 30, the end cap 90 is placed onto the front portion 92. As should be appreciated, the placement of the end cap 90 onto the front portion 92 after use of the body fluid testing device 30 ensures a safe and hygienic disposal of the testing device 30 by enclosing the front portion 92 that may be contaminated with body fluid.

Figure 11:
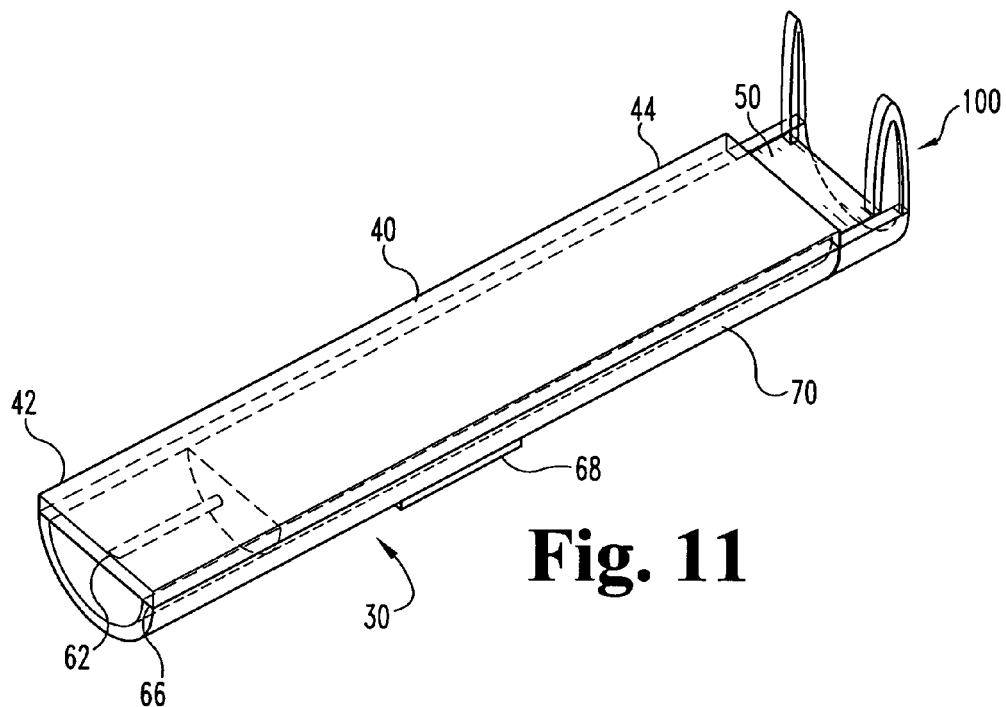
FIG. 11 is a perspective view of the FIG. 10 device in a retracted position.
Figure 10:
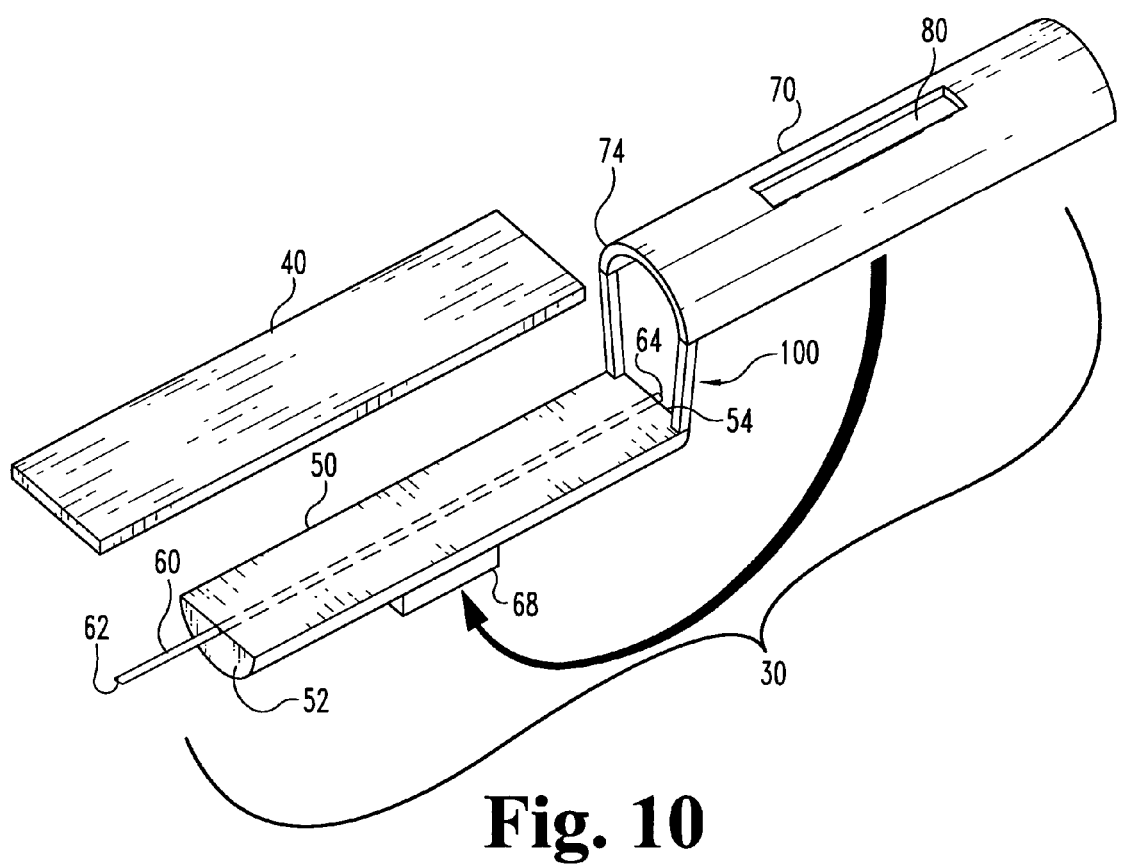
FIG. 10 is an exploded view of a body fluid testing device according to a third embodiment.

FIGS. 10 and 11 illustrate the body fluid testing device 30 according to an alternate embodiment of the present invention. As depicted in FIG. 10, the incision forming member 50 and the housing 70 are detachably molded to form one body. In the illustrated embodiment, the incision forming member 50 is attached to the housing 70 via a pair of connectors 100. The pair of connectors 100 are made of any material that allows the incision forming member 50 to detach or separate from the housing 70. By way of non-limiting examples, the connectors 100 may be made of a flexible plastic material or rubber, to name a few. In one embodiment, during the manufacturing process, the housing 70 will be rotated such that the opening 80 aligns over the tab 68 of the incision forming member 50. In another embodiment, in operation of the body fluid testing device 30 the user will rotate the housing 70 such that the opening 80 aligns over the tab 68 of the incision forming member 50. The opening 80 receives the tab 68. The test strip 40 attaches to the housing 70. As illustrated in FIG. 11, the needle tip 62 is retracted beyond the skin contacting portion 42 towards the distal portion 44 of the test strip 40. In one form, the pair of connectors 100 are removed from the incision forming member 50 and the housing 70 to detach the end portion 54 of the incision forming member 50 from the second portion 74 of the housing 70. In another form, the pair of connectors 100 are severed to detach the end portion 54 of the incision forming member 50 from the second portion 74 of the housing 70. As should be appreciated, the removal and/or severance of the pair of connectors 100 frees the movement of the incision forming member 50 with respect to the housing 70. However, in other forms, the pair of connectors 100 are configured to allow unlimited movement of the incision forming member 50 with respect to the housing 70.

Figure 12:
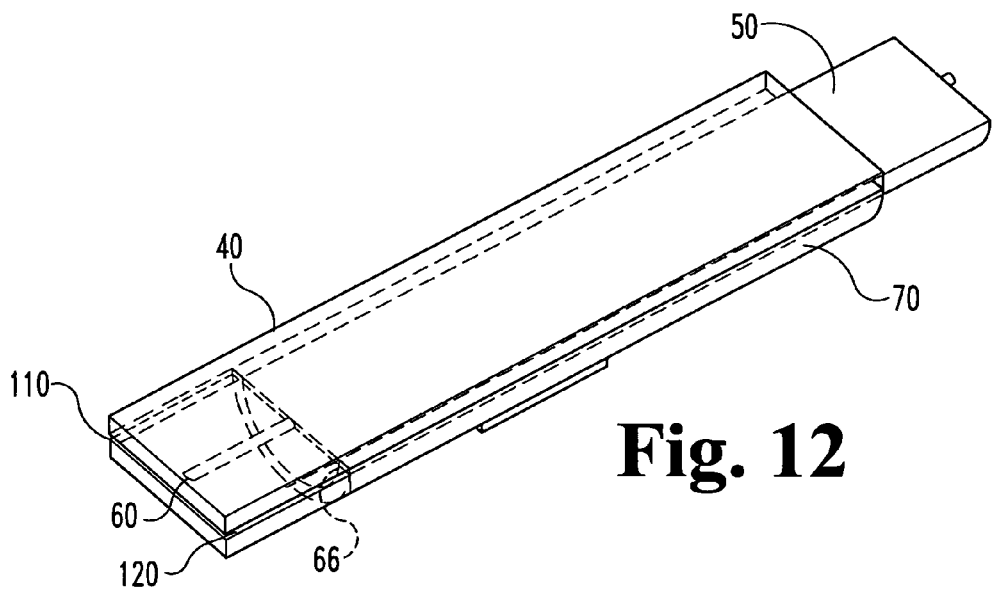
FIG. 12 is a perspective view of a body fluid testing device according to a fourth embodiment.
Figure 13:
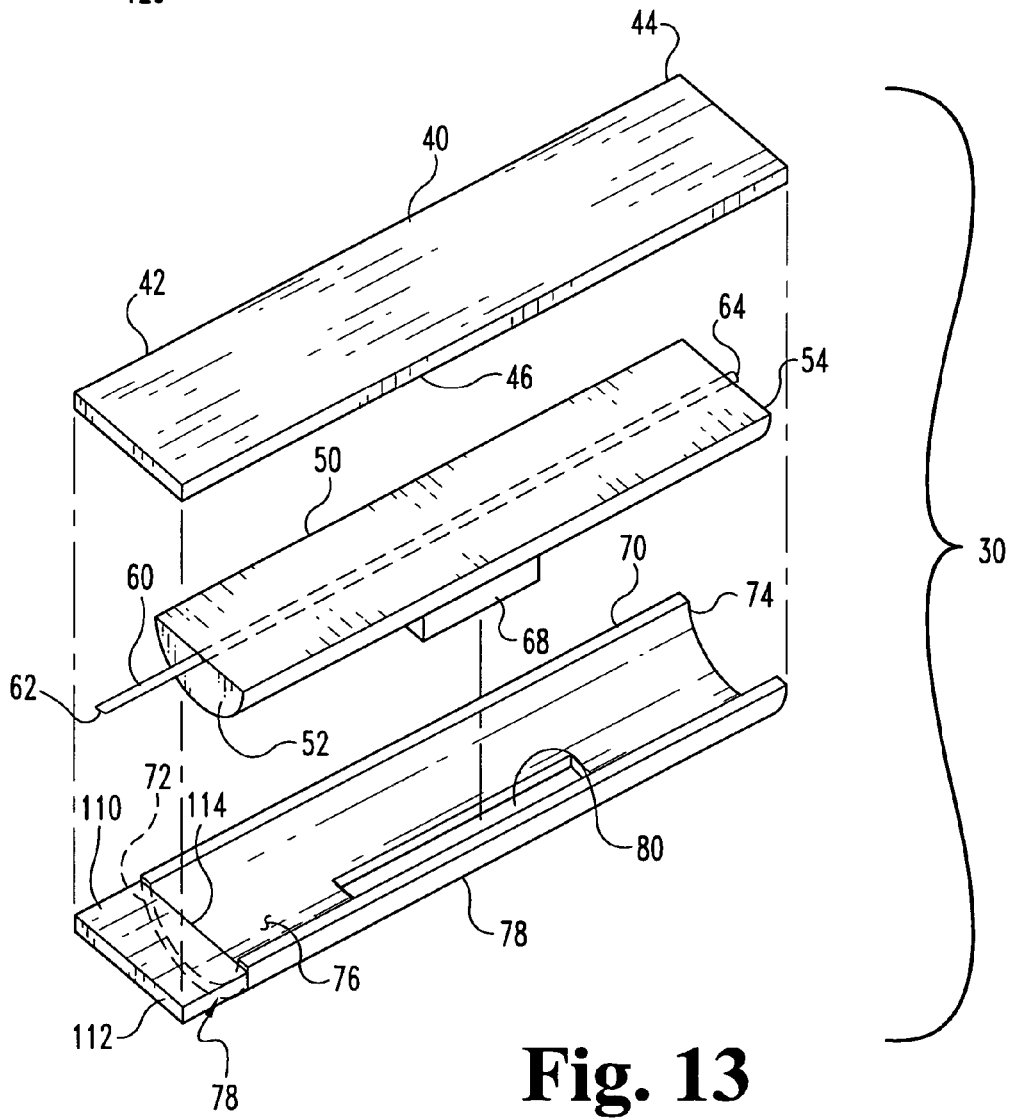
FIG. 13 is an exploded view of the FIG. 12 device.

In an alternate embodiment, illustrated in FIGS. 12 and 13, the body fluid testing device 30 includes an extension 110. Extension 110 has a skin contacting portion 112 for contacting skin and a distal portion 114 for contacting first portion 72. Extension 110 extends from first portion 72 to align with skin contacting portion 42 of test strip 40. In one form, extension 110 and test strip 40 are aligned in a parallel relationship. The incision forming member 50 is configured to slidably engage within cavity 66 however the sampling portion 52 can not extend beyond the distal portion 114. The alignment of extension 110 and test strip 40 forms a passageway 120. In one form, the passageway 120 is sized to draw fluid via capillary action or affinity. In another form, the passageway 120 is sized such that test strip surface 46 draws fluid. Different materials may have different affinities for a fluid, such that forming the expression surface 46 and the extension 110 from different materials will provide a change in the capillary affinity between those portions. Treating or coating the expression surface 46 to provide a resulting surface that is more or less hydrophilic changes the capillary affinity. The capillary affinity could also be changed by treating or coating the extension 110 to provide a resulting surface that is more or less hydrophilic. The present invention is operable in respect to any way in which the capillary affinity is varied.

Figure 14:
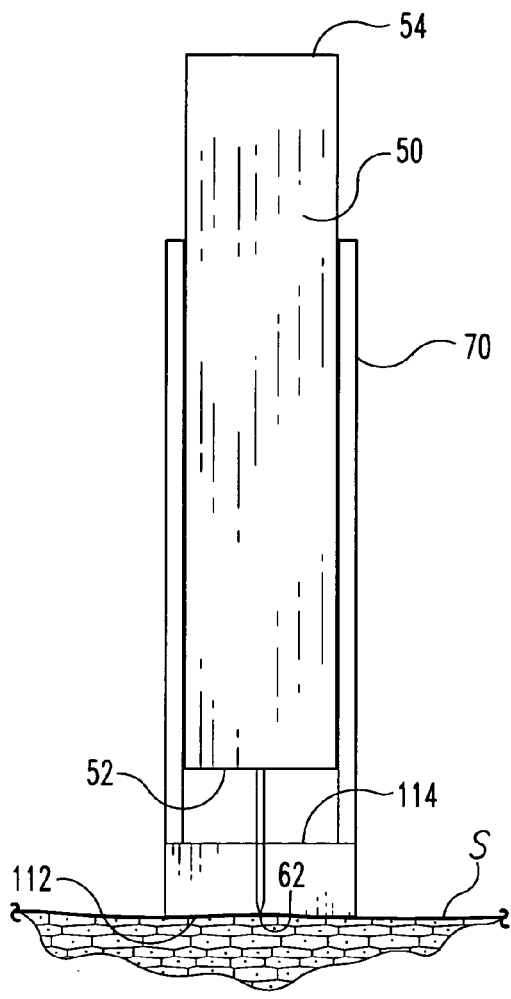
FIG. 14 is a rotated view of the FIG. 12 device before the incision is formed in the skin.
Figure 15:
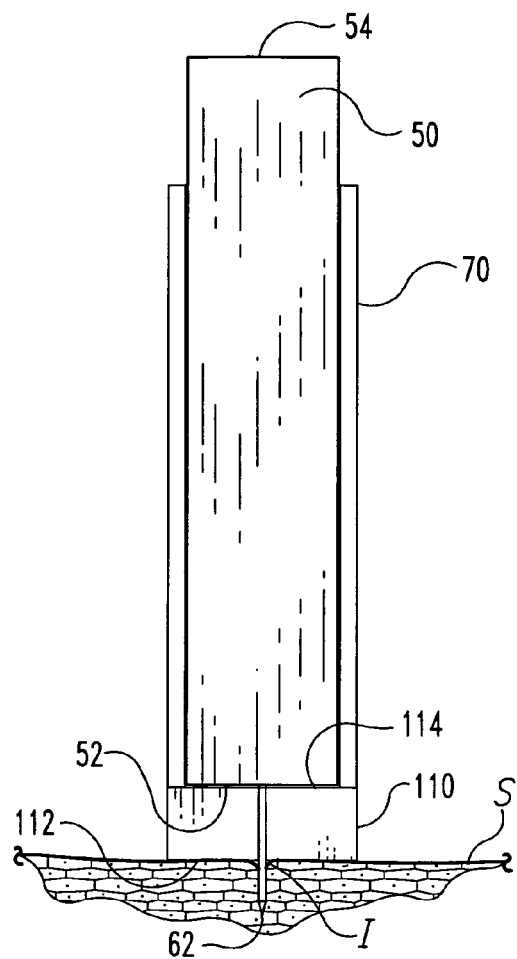
FIG. 15 is a rotated view of the FIG. 12 device forming an incision in the skin.

The operation of the body fluid testing device 30 will now be described with reference to FIGS. 12, 14, and 15. In FIGS. 14 and 15, the test strip 40 has been removed for clarity. FIGS. 12 and 14 illustrate the relative position of the incision forming member 50 such that the needle tip 62 is retracted beyond the skin contacting portion 112 towards distal portion 114 before the body fluid testing device 30 is placed on the user's skin S. The incision forming member 50 is retracted by retraction mechanisms wherein the retraction mechanism is coupled to the tab 68 to retract the incision forming member 50. In another form, the retraction mechanism is coupled to the end portion 54 to retract the incision forming member 50. The opening 80 that receives the tab 68 limits the motion or movement of the incision forming member 50. The skin contacting portion 42 is placed against the skin S. FIG. 15 illustrates the relative position of incision forming member 50 after the end portion 54 is driven toward the sampling portion 52 thereby driving the needle tip 62 through the passageway 120 and into the user's skin S with the needle tip 62 to form an incision I. The needle tip 62 or another device to form an incision in skin extends through passageway 120 beyond extension 110 to form an incision in skin. The incision forming member 50 can be actuated or driven toward the skin S using actuation mechanisms of a lancing device. The actuation mechanism can be coupled to the tab 68 or the end portion 54 to drive the incision forming member 50 towards the skin S. Also illustrated in FIG. 14, is the needle tip 62 withdrawn from the skin S and the sampling portion 52 is retracted towards the end portion 54.

Figure 16:
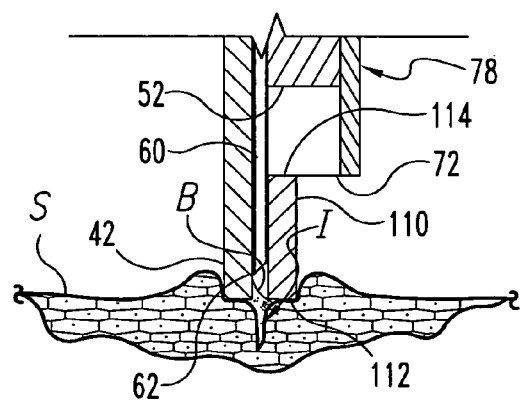
FIG. 16 is a rotated view of the FIG. 12 device during expression of fluid from the skin.

FIG. 16 illustrates expressing bodily fluid from incision I according to one embodiment where the skin contacting portion 42 and the skin contacting portion 112 remain in contact with the skin S. After the sampling portion 52 is retracted from the skin S, the body fluid B is expressed from the incision I. The skin contacting portion 42 and the skin contacting portion 112 express body fluid B from the incision I, such as by applying pressure to the skin S surrounding the incision I to milk or pump the fluid B from the incision I. The body fluid B is drawn onto the test strip 40 for testing via the capillary action of the passageway 120. After the body fluid B is expressed, the expression surface 46 of the test strip 40 collects the body fluid B.

In another embodiment, illustrated in FIGS. 19, 20, 21 and 22, the body fluid testing device 30 includes a cover 130 to attach the test strip 40 to the housing 70. Cover 130 extends from the second portion 74 towards the first portion 72 of the housing 70. In the illustrated embodiment, the cover 130 is adhesively attached to the housing 70. By way of nonlimiting examples, cover 130 can be attached to the housing 70 by a clamp mechanism, welding, and/or by a snap mechanism, to name a few. The incision forming member 50 is configured to slidably engage within passageway 140. The alignment of test strip 40 and housing 70 forms a passageway 140. In one form, the passageway 140 is sized to draw fluid via capillary action or affinity. In another form, the passageway 140 is sized such that test strip surface 46 draws fluid. Different materials may have different affinities for a fluid, such that forming the expression surface 46 and the sampling portion 52 from different materials will provide a change in the capillary affinity between those portions. Treating or coating the expression surface 46 to provide a resulting surface that is more or less hydrophilic changes the capillary affinity. The capillary affinity could also be changed by treating or coating the expression surface 46 to provide a resulting surface that is more or less hydrophilic. The present invention is operable in respect to any way in which the capillary affinity is varied.

Figure 21:
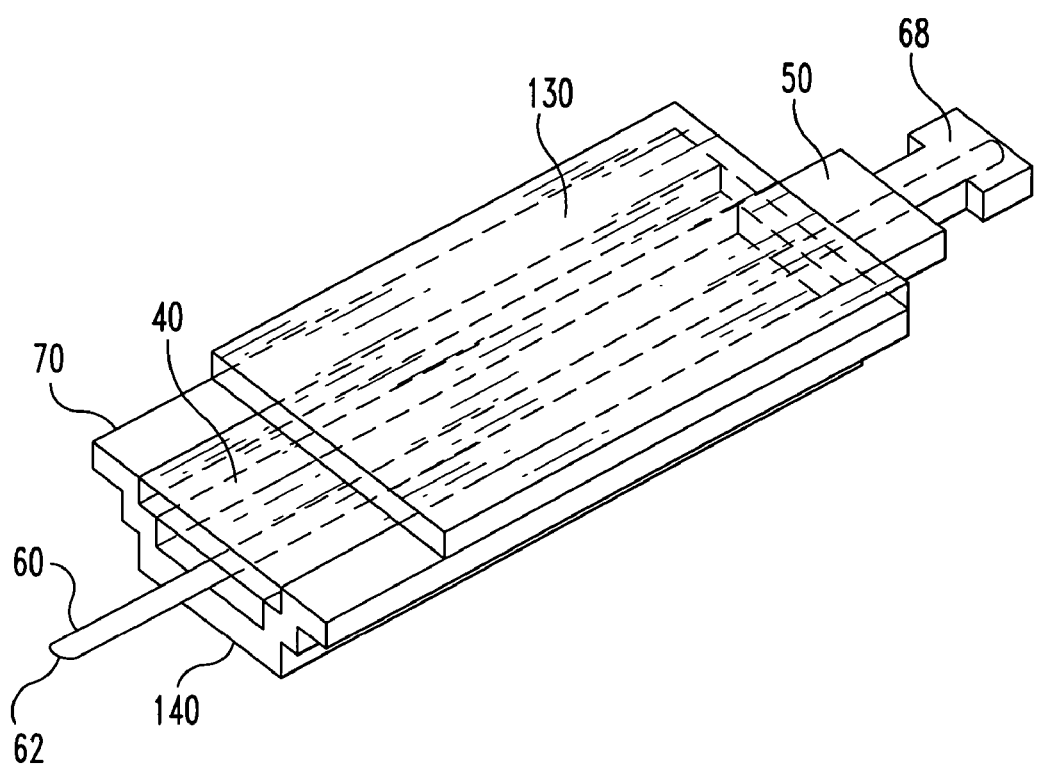
FIG. 21 is a perspective view of the FIG. 19 device in an extended position.
Figure 22:
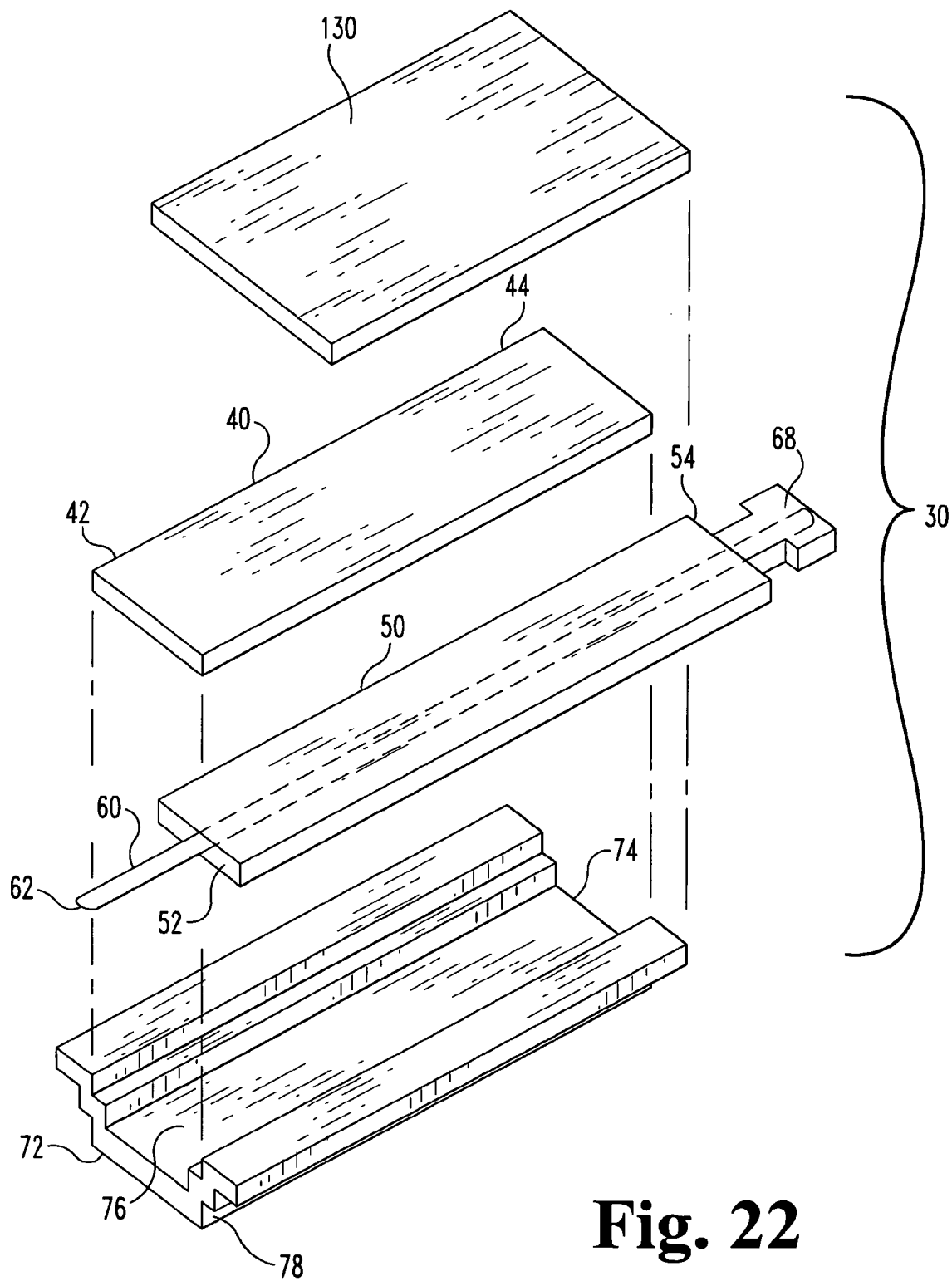
FIG. 22 is an exploded view of the FIG. 19 device.

As shown in FIG. 21, the incision forming member 50 includes a tab 68. A retraction mechanism or an actuation mechanism is coupled to the tab 68 to limit the motion or movement of the incision forming member 50 in the passageway 140. In the illustrated embodiment in FIG. 23, a retraction mechanism 51 has an arm 53 that is coupled to the tab 68 to retract the incision forming member 50. The test strip 40 in FIGS. 23 and 24 is removed for clarity. In operation, the arm 53 of the retraction mechanism 51 retracts the needle tip 62 beyond the skin contacting portion 42 towards the distal portion 44 of the test strip 40. As shown in FIG. 24, an actuation mechanism 61 has an arm 63 that is coupled to the tab 68 to actuate the incision forming member 50. The arm 63 of the actuation mechanism 61 is coupled to the tab 68 to drive the incision forming member 50 towards the skin S to form an incision I in the user's skin with the needle tip 62. After an incision I in the skin S is formed, the needle tip 62 is withdrawn from the user's skin S by retracting the incision forming member 50. In the illustrated form, the incision forming member 50 is retracted by the arm 53 of the retraction mechanism 51 as shown in FIG. 23. The arm 53 of the retraction mechanism 51 is attached to the tab 68 to move the tab 68 thereby removing the needle tip 62 from the user's skin S and retracting the incision forming member 50.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus, comprising:
   a disposable body fluid testing cartridge including
   an incision forming member for forming an incision in skin, the incision forming member having a tab that extends laterally from the incision forming member for controlling movement of the incision forming member as the incision forming member is extended and retracted during formation of the incision, a housing defining a side opening through which the tab extends for controlling penetration depth of the incision forming member into the skin, connectors attaching the incision forming member to the housing to form one molded body, the connectors being flexible to facilitate folding of the incision forming member against the housing, wherein the connectors are positioned to align the tab of the incision forming member with the opening in the housing as the incision forming member and housing are folded together about the connectors, the incision forming member and the housing being folded together with the connectors being bent, the tab of the incision forming member extending laterally through the opening of the housing, the opening of the housing configured to limit movement of the tab, a test strip attached to the housing for analyzing body fluid from the incision in the skin, the test strip having an expression surface configured to express the body fluid from the incision when pressed against the skin, wherein the housing has a first cavity wall and the test strip has a second cavity wall, the first cavity wall of the housing and the second cavity wall of the test strip defining a capillary cavity configured to draw body fluid onto the test strip via capillary action, the incision forming member being slidably disposed within said capillary cavity; and an actuation mechanism coupled to the tab of the incision forming member for extending and retracting the incision forming member during formation of the incision, the actuation mechanism coupled to the exterior of the housing to engage the tab being extended through the opening.

2. The apparatus of claim 1, wherein the connectors are configured to permit movement of the incision forming member relative to the housing.

3. The apparatus of claim 1, wherein the connectors are severed to permit movement of the incision forming member relative to the housing.

4. The apparatus of claim 1, wherein the housing that in part defines the capillary cavity has a half-pipe shape to simplify manufacturing.

5. The apparatus of claim 4, wherein the housing has a pair of edges defined by the half-pipe shape and the test strip is coupled to the pair of edges of the housing.

6. The body fluid testing device of claim 1, wherein the expression surface is coated with a hydrophilic material to promote fluid collection.

7. The apparatus of claim 1, wherein the housing includes an extension configured to contact skin, the extension including the first cavity wall.

8. The body fluid testing device of claim 1, wherein the incision forming member includes a needle.

9. The body fluid testing device of claim 1, wherein the incision forming member is coated with a hydrophilic material to promote fluid collection.

10. The body fluid testing device of claim 1, further comprising:

a cap covering the incision forming member to protect the sterility of the incision forming member; and wherein the incision forming member, the test strip, and the housing are configured to receive the cap.

11. An apparatus, comprising:

a disposable body fluid testing cartridge including an incision forming member for forming an incision in skin, a housing for receiving the incision forming member, connectors molded with the incision forming member and the housing to form one body, the connectors being flexible to facilitate folding of the incision forming member against the housing, the incision forming member and the housing being folded together with the connectors being bent, a test strip attached to the housing for analyzing body fluid from the incision in the skin, the test strip having an expression surface configured to express the body fluid from the incision when pressed against the skin, wherein the housing has a first cavity wall and the test strip has a second cavity wall, the first cavity wall of the housing and the second cavity wall of the test strip defining a capillary cavity configured to draw body fluid onto the test strip via capillary action, the incision forming member being slidably disposed within said capillary cavity, wherein the housing defines a guide opening along one side, wherein the incision forming member having a tab extending laterally through the guide opening in the housing, the guide opening of the housing configured to limit movement of the tab, wherein the connectors are positioned to align the tab of the incision forming member with the guide opening in the housing, and an actuation mechanism coupled to the tab of the incision forming member for extending and retracting the incision forming member during formation of the incision, the actuation mechanism coupled to the exterior of the housing to engage the tab through the guide opening.

12. The apparatus of claim 11, wherein the connectors are configured to disconnect from the incision forming member to permit movement of the incision forming member relative to the housing.

13. The apparatus of claim 11, wherein the connectors are configured to permit movement of the incision forming member relative to the housing.

14. The apparatus of claim 11, further comprising:

a cap covering the incision forming member to protect the sterility of the incision forming member; and wherein the incision forming member, the test strip, and the housing are configured to receive the cap.

15. An apparatus, comprising:

a disposable body fluid testing cartridge including an incision forming member for forming an incision in skin, a housing defining a side, guide opening for guiding the incision forming member during penetration into the skin, a tab extending laterally from the incision forming member through the guide opening in the housing for controlling penetration depth of the incision forming member as the incision forming member is extended and retracted during formation of the incision, the guide opening configured to limit movement of the incision forming member, a test strip attached to the housing for analyzing body fluid from the incision in the skin, the test strip having an expression surface configured to express the body fluid from the incision when pressed against the skin, wherein the housing has a first cavity wall and the test strip has a second cavity wall, the first cavity wall of the housing and the second cavity wall of the test strip defining a capillary cavity configured to draw body fluid onto the test strip via capillary action, the incision forming member being slidably disposed within said capillary cavity, and an actuation mechanism coupled to the tab of the incision forming member for extending and retracting the incision forming member during formation of the incision, the actuation mechanism coupled to the exterior of the housing to engage the tab through the guide opening.

16. The apparatus of claim 15, wherein the incision forming member and the housing are molded to form one body.

17. The apparatus of claim 15, further comprising:
connectors attaching the incision forming member to the housing, the connectors being flexible to facilitate folding of the incision forming member against the housing, wherein the connectors are positioned to align the tab of the incision forming member with the opening in the housing as the incision forming member and housing are folded together about the connectors.

* * * * *

UNITED STATES PATENT AND TRADEMARK OFFICE
CERTIFICATE OF CORRECTION

| | | |
|---|---|---|
| PATENT NO. | : 7,766,845 B2 | |
| APPLICATION NO. | : 10/872945 | |
| DATED | : August 3, 2010 | |
| INVENTOR(S) | : Detlef Thym | |

It is certified that error appears in the above-identified patent and that said Letters Patent is hereby corrected as shown below:

Title page 2, Item [56] U.S. PATENT DOCUMENTS, add "6,136,013 A*   10/2000   Marshall et al."

Signed and Sealed this
Fifth Day of June, 2012

David J. Kappos
*Director of the United States Patent and Trademark Office*